United States Patent [19]
Hausheer et al.

[11] Patent Number: 5,880,133
[45] Date of Patent: Mar. 9, 1999

[54] PHARMACEUTICAL FORMULATIONS OF HIGHLY LIPOPHILIC CAMPTOTHECIN DERIVATIVES

[75] Inventors: Frederick H. Hausheer; Kochat Haridas; Dhanabalan Murali; Dasharatha Gauravaram Reddy, all of San Antonio, Tex.

[73] Assignee: BioNumerik Pharmaceuticals, Inc., San Antonio, Tex.

[21] Appl. No.: 667,424

[22] Filed: Jun. 21, 1996

Related U.S. Application Data

[63] Continuation-in-part of Ser. No. 461,385, Jun. 5, 1995.
[51] Int. Cl.$^6$ .................................................. A61K 31/475
[52] U.S. Cl. ................................................ 514/283
[58] Field of Search ............................................ 514/283

[56] References Cited

U.S. PATENT DOCUMENTS

| | | |
|---|---|---|
| 4,473,692 | 9/1984 | Miyasaka et al. . |
| 4,772,589 | 9/1988 | Kaplan et al. . |
| 4,778,891 | 10/1988 | Tagawa et al. . |
| 5,034,397 | 7/1991 | Kaplan et al. . |
| 5,061,800 | 10/1991 | Yaegashi et al. . |
| 5,422,361 | 6/1995 | Munayyer et al. ...................... 514/408 |
| 5,447,936 | 9/1995 | Hausheer et al. ........................ 514/283 |
| 5,468,754 | 11/1995 | Hausheer et al. ........................ 514/283 |
| 5,573,781 | 11/1996 | Brown et al. ............................ 424/484 |

FOREIGN PATENT DOCUMENTS

90/14094  11/1990  WIPO .

OTHER PUBLICATIONS

Barilero, et al., Simultaneous determination of the camptothecin analogue CPT–11 and its active metabolite SN–38 by high–performance liquid chromatography: application to plasma pharmacokinetic studies in cancer patients, Journal of Chromatography, 575 (1992) 275–280.
Bates, T. et al., Solubilizing Properties of Bile Salt Solutions I. Effect of Temperature and Bile Salt Concentration on Solubilization of Glutethimide, Griseofulvin, and Hexestrol. Journal of Pharmaceutical Sciences 55:191–199, (1966).
Bates, T. et al., Rates of Dissolution of Griseofulvin and Hexestrol in Bile Salt Solutions, Chemical Abstracts, 65:8680b, 1966.
Bates, et al., Solubilizing Properties of Bile Salt Solutions on Glutethimide, Griseofulvin, and Hexestrol. Chem. Abstracts 64: 9517e 1966; 65:15165a, 1966.
Clavel, M. et al., Phase I Study of the Camptothecin Analoigue CPT–11, Administered Daily for 3 Consecutive Days. Proc. Amer. Assoc. Cancer Res. 3:83, 1992.
Creaven, P.J. et al., Plasma Camptothecin (NSC–100880) Levels During a 5–Day Course of Treatment: Relation to Dose and Toxicity. Cancer Chem. Rep. 56: 573–578, 1972.
Culine, S., Phase I Study of the Camptothecin Analog CPT–11, Using a Weekly Schedule. Proc. Of Amer. Soc. Clin. Onc. 11:110, 1992.

Emerson, D.L., In Vivo Antitumor Activity of Two New Seven–substituted Water–soluble Camptothecin Analogues. Cancer Research. 55: 603–609, 1995.
Fukuoka, M. et al., A Phase II Study of CPT–11, A New Derivative of Camptothecin, for Previously Untreated Small–Cell Lung Cancer. J. Clin. Onc. 10(1): 16–20, 1992.
Giovanella, B.C., et al. DNA Topoisomerase I—Targeted Chemotherapy of Human Colon Cancer in Xenografts. Science 246: 1046–1048; 1989.
Gottlieb, J.A. et al., Preliminary Pharmacologic and Clinical Evaluation of Camptothecin Sodium (NSC–100880). Cancer Chem. Rep. 54: 461–470, 1970.
Gottlieb, J.A. et al., Treatment of Malignant Melanoma with Camptothecin (NSC–100880). Cancer Chem. Rep. 56: 103–105, 1972.
Hsiang et al., Arrest of Replication Forks by Drug–stabilized Topoisomerase I–DNA Cleavable Complexes as a Mechanism of Cell Killing by Camptothecin Analogues. Cancer Res. 49:5077–5082, 1989.
Houghton, P.J: et al., Therapeutic Efficacy of the Topoisomerase I Inhibitor 7–Ethyl–10–(4–[1–piperidino]–1–piperidino)–carbonyloxy–camptothecin against Human Tumor Xenografts: Lack of Cross–Resistance in Vivo in Tumors with Acquired Resistance to the Topoisomerase I Inhibitor 9–Dimethylaminomethyl–10–hydroxycamptothecin. Cancer Res. 53:2823–2829, 1993.
Jaxel, C. et al., Structure Activity Study of the Actions of Camptothecin Derivatives on Mammalian Topoisomerase I: Evidence for a Specific Receptor Site and a relation to Antitumor Activity. Cancer Res. 49: 1465–1469, 1989.
Kaneda, N. et al., Metabolism and Pharmacokinetics of the Camptothecin Analogue CPT–11 in the Mouse. Cancer Research 50:1715–1720, 1990.
Kano, Y., et al., Effects of CPT–11 in Combination with other Anti–Cancer Agents in Cluture. Int. J. Cancer 50:604–610; 1992.
Kanzawa, F., et al., Role of Carboxylesterase on Metaolism of Camptothecin Analog (CPT–11) in Non–Small Cell Lung Cancer Cell Line PC–7 Cells (Meeting Abstract). Proc. Annual Meet. Am. Assoc. Cancer Res. 33:A2552; 1992.
Kawato, Y., et al., Intracellular Roles of SN38, a Metabolite of the Camptothecin Derivative CPT–11, in the Antitumor Effect of CPT–11. Cancer Res. 51:4187–4191, 1991.
Kunimoto, T. et al., Antitumor Activity of 7–Ethyl–10–[4–(1–piperidino)–1–piperidino]Carbonyloxy–Camptothecin, a Novel Water Soluble Derivative of Camptothecin Against Murine Tumors. Cancer Res. 47:5944–5947, 1987.
Luzzio, M.J., et al., Synthesis and Antitumor Activity of Novel Water Soluble Derivatives of Camptothecin as Specific Inhibitors of Topoisomerase I. J. Med. Chem. 38: 395–401, 1995.

(List continued on next page.)

*Primary Examiner*—Rebecca Cook
*Attorney, Agent, or Firm*—Thomas J. Dodd

[57] ABSTRACT

Pharmaceutical formulations of Highly Lipophilic Camptothecin Derivatives (HLCD) include HLCD dissolved in N-methyl Pyrrolidinene (NMP). The formulations also include quantities of pharmaceutically acceptable excipients and diluents incorporated thereinto.

12 Claims, No Drawings

OTHER PUBLICATIONS

Malone et al., Desoxycholic Acid Enhancement of Orally Administered Reserpine. Journal of Pharmaceutical Sciences, 55:972–974 (1966).

Masuda, N., et al., CPT–11: A New Derivative of Camptothecin for the Treatment of Refractory or Relapsed Small–Cell Lung Cancer. J. Clin. Onc. 10(8): 1225–1229, 1992.

Moertel, C.G. et al., Phase II Study of Camptothecin (NSC–100880) in the Treatment of Advanced Gastrointestinal Cancer. Cancer Chem. Rep. 56: 95–101, 1972.

Muggia, F.M. et al., Phase I Clinical Trial of Weekly and Daily Treatment with Camptothecin (NSC–100880): Correlation with Preclinical Studies. Cancer Chem. Rep. 56:515–521, 1972.

Negoro, S. et al., Phase I Study of Weekly Intravenous Infusions of CPT–11, a New Derivative of Camptothecin, in the Treatment of Advanced Non–Small Cell Lung Cancer. JNCI 83(16): 1164–1168, 1991.

Negoro, S., et al., Phase II Study of CPT–11, New Camptothecin Derivative, in Small Cell Lung Cancer. Proc. Of Amer. Soc. Clin. Onc. 10:241, 1991.

Niimi, S., et al., Mechanism of Cross–Resistance to a Camptothecin Analogue (CPT–11) in a Human Ovarian Cancer Cell Line Selected by Cisplatin. Cancer Res. 52: 328–333; 1992.

Ohe, Y., et al., Phase I Study and Pharmacokinetics of CPT–11 with 5–Day Continuous Infusion. JNCI 84(12): 972–974, 1992.

Ohno, R. et al., An Early Phase II Study of CPT–11: A New Derivative of Camptothecin, for the Treatment of Leukemia and Lymphoma. J. Clin. Onc. 8(11): 1907–1912, 1990.

Pantazis, P. et al., Cytotoxic Efficacy of 9–Nitrocamptothecin in the Treatment of Human Malignant Melanoma Cells in Vitro. Cancer Research. 54: 771–776, 1994.

Pommier, Y. et al., Camptothecins: Mechanism of Action and Resistance (Meeting Abstract). Cancer Investigation, Presented at the "Chemotherapy Foundation Symposium X Innovative Cancer Chemotherapy for Tomorrow", p. 3, 1992.

Potmesil, M. et al., Preclinical and Clinical Development of DNA Topoisomerase I Inhibitors in the United States. In Andoh, T., Ikeda, H., Oguro, M. (editors): Molecular Biology of DNA Topoisomerases and Its Application to Chemotherapy. Boca Raton, FL, CRC Press, Inc. 301–311, 1993.

Rivory, L.P., et al., Kinetics of the in Vivo Interconversion of the Carboxylate and Lactone Forms of Irinotecan (CPT–11) and of Its Metabolite SN–38 in Patients. Cancer Research. 54:6330–6333, 1994.

Rothenberg, M.L. et al., A Phase I and Pharmacokinetic Trial of CPT–11 in Patients with Refractory Solid Tumors. Amer. Soc. Clin. Onc. 11:113, 1992.

Rothenberg, M.L., Kuhn, J.G., Burris, H.A., Nelson, J., Eckardt, J.R., Tristan–Morales, M., Hilsenbeck, S.G., Weiss, G.R., Smith, L.S., Rodriguez, G.I., Rock, M.K., Von Hoff, D.D. Phase I and Pharmacokinetic Trial of Weekly CPT–11. Journal of Clinical Oncology. 11:2194–2204 (1993).

Rowinsky, E. et al., Phase I Pharmacologic Study of CPT–11, A Semisynthetic Topoisomerase I–Targeting Agent, on a Single–Dose Schedule (Meeting Abstract). Proc. Of Amer. Soc. Clin. Onc. 11:115, 1992.

Sawada, S., et al., Synthesis and Antitumor Activity of 20 (S) – Camptothecin Derivatives: Carbonate–Linked, Water Soluble, Derivatives of 7–Erthyl–10–hydroxycamptothecin. Chem. Pharm. Bull. 39:1446–1454; 1991.

Shimada, Y. et al., Phase II Study of CPT–11, New Camptothecin Derivative, In the Patients with Metastatic Colorectal Cancer. Proc of Amer. Soc. Clin. Onc. 10:135, 1991.

Supko, J.G. et al., Pharmacokinetics of the 9–Amino and 10,11–Methylenedioxy Derivatives of Camptothecin in Mice. Cancer Research 53: 3062–3069, 1993.

Takeuchi, S. et al., Late Phase II Study of CPT–11, A Topoisomerase I Inhibitor, In Advanced Cervical Carcinoma (CC) (Meeting Abstract). Proc. Of Amer. Soc. Clin. Onc. 11:224, 1992.

Wall, M.E. et al., Camptothecin and Taxol: Discovery to Clinic–Thirteenth Bruce F. Cain Memorial Award Lecture. Cancer Research. 55:753–760, 1995.

Wall, M.E, et al., Camptothecin, in Cassady J.M., Douros, J.D. (eds): Anticancer Agents Based on Natural Product Models, San Diego, CA, Academic Press, 1980, 417–436.

Wall, M.E. et al., Plant Antitumor Agents: Synthesis and Structure Activity of Novel Camptothecin Analogs. J. Med. Chem., 36:2689–2700 (1993).

Westergaard et al., The Mechanism Whereby Bile Acid Micelles Increase the Rate of Fatty Acid and Cholesterol Uptake Into the Intestinal Mucosal Cell. Journal of Clinical Investigation, 58: 97–108 (1976).

PHARMACEUTICAL FORMULATIONS OF HIGHLY LIPOPHILIC CAMPTOTHECIN DERIVATIVES

CROSS-REFERENCE TO RELATED APPLICATIONS

This application is a continuation-in-part of co-pending application, Ser. No. 08/461,385, filed Jun. 5, 1995.

FIELD OF THE INVENTION

This invention relates to useful, novel and non-obvious formulations of camptothecin derivatives, and will have particular application to formulations of poorly water soluble (<5 µg/ml) camptothecin derivatives.

BACKGROUND OF THE INVENTION

For the purpose of this invention, poorly water soluble and highly lipophilic camptothecin derivatives (referred to as "HLCD" for the purposes of this invention) are defined interchangeably as any unsubstituted or any A-ring and/or B-ring substituted camptothecin which has a water solubility of less than 5 micrograms per milliliter (<5 µg/mL) of water. Also for the purposes of the instant invention, the terms "highly lipophilic" and "poorly water soluble" are used interchangeably to describe the fundamental bioavailability and chemical behavior of the camptothecin derivatives.

Utilizing HPLC and NMR techniques, researchers have demonstrated that camptothecin and many of its derivatives undergo an alkaline, pH-dependent hydrolysis of the E-ring lactone. The slow reaction kinetics allow one to assess whether both the lactone and non-lactone forms of the drug stabilize the topoisomerase I-cleaved DNA complex. Studies indicate that only the closed lactone form of the drug helps stabilize the cleavable complex. This observation provides reasoning for the high degree of drug activity observed in solid tumor models. Tumor cells, particularly hypoxic cells prevalent in solid neoplasms, have relatively lower intracellular pH levels than normal cells. At pH levels below 7.0, the lactone E-ring form of camptothecin predominates.

Formulations of camptothecin and its derivatives in the lactone form are difficult to prepare, due to the factors cited above. The poor solubility of these compounds in aqueous solution prohibits administration of effective doses. The opening of the lactone ring in alkaline formulations precludes their utility as well, due to a substantial reduction in the anti-tumor potency of the compounds.

The prior art teaches the use of various organic solvents useful for camptothecin formulations. This prior art is identified in the Information Disclosure Statement accompanying this application. Such solvents include lipid-based oils, such as cottonseed oil, peanut oil, IL-20 and others, and organic solvents such as N,N-dimethylacetamide (DMA), dimethylisosorbide (DMI), and others. Solubility of the compounds in lipid-based solvents is generally less than 1 mg/mL, while the solubility increases to as high as about 6.7 mg/mL in certain organic solvents.

SUMMARY OF THE INVENTION

The formulations of this invention include as the primary solvent the compound N-methylpyrrolidin-2-one, also referred to as N-methylpyrrolidinone, or simply, NMP. The solubility of highly lipophilic, poorly water soluble camptothecin derivatives is increased to between 15.0 and 20.0 mg/mL in NMP, which allows for much more concentrated solutions to be prepared in advance of formulating. The resulting higher drug concentration attained by the instant invention allows greater utility for preparing oral and parenteral formulations.

The preferred formulations of this invention include the following: [a] HLCD; [b] NMP; [c] polyethylene glycol (PEG) or propylene glycol; [d] an acid; [e] a non-ionic surfactant; and [f] a low MW alcohol. In addition, certain formulations may also include [g] a heavy oil, such as epoxylated castor oil; [h] glycerol; and [i] taurocholic acid or a pharmaceutically acceptable salt thereof, or a similar intestinal absorption enhancing agent.

The solutions and formulations of this invention are able to contain a high concentration of effective ingredient due to the unpredictably high solubility of the compounds in NMP. This allows a lower solvent volume delivery to the patient to deliver the same amount of effective ingredient, which in turn results in reduced risk of toxicity and greater patient acceptance.

The formulations of this invention can be tailored for various types of delivery, including parenteral, subcutaneous and oral, among others. Specific examples of oral and parenteral formulations are given in the detailed description which follows.

DETAILED DESCRIPTION OF THE INVENTION

The preferred formulations disclosed below are not intended to be exhaustive or to limit the invention to the precise forms disclosed. Rather, they have been chosen and described to explain the principles of the invention, and their application and practical use to best enable others skilled in the art to follow its teachings.

The pharmaceutical formulations which comprise this invention include as basic ingredients, a pharmaceutically effective amount of a highly lipophilic camptothecin derivative (HLCD) dissolved or suspended in N-methylpyrrolidin-2-one (NMP). The solubility of most HLCDs in NMP is between 15.0 and 25.0 mg/mL. In formulating solutions it is desirable to use enough NMP to completely dissolve the HLCD prior to adding any other excipients or diluents. Approximate ratios for formulating solutions are between 25 parts by weight to 1,000 parts by weight NMP per part by weight of HLCD, preferably between 50 to 500 parts by weight NMP per part HLCD, and most preferably between 100 to 300 parts by weight NMP per part HLCD. In the most preferred case, this will yield an initial NEAT solution concentration of about 1 mg/mL to about 40 mg/mL.

Suspensions, typically employed in orally administered formulations, may include significantly higher concentrations, up to 400 mg/mL of the NEAT formulation.

Other pharmaceutically acceptable diluents and excipients may also be included in the preferred formulations, as outlined below. Typically, a pharmaceutical formulation of HLCD will include from 1.0 to 40.0 mg of HLCD per mL of solution or 1 mg/mL to 400 mg/mL suspension.

The pharmaceutically acceptable excipients and diluents preferably will be chosen from the following groups, keeping in mind that the exact nature of the formulation will depend upon the intended method of delivery.

One of the pharmaceutically acceptable excipients included in the formulation is a pharmaceutically acceptable acid, which is included to lower the pH of the formulation to between 2.0–6.0 (most preferably between 3.0–5.0) to keep the HLCD in its active lactone configuration. The preferred acid may be chosen from any one of a number of pharmaceutically acceptable mineral acids or organic acids, including hydrochloric acid, phosphoric acid, tartaric acid, lactic acid, ascorbic acid, citric acid, gluconic acid, fumaric acid, maleic acid and others. The acid will preferably be employed at the ratio of 10 to 5,000 parts by weight of the HLCD, most preferably between 100 to 2,500 parts by weight per part of HLCD. Citric acid is the most preferred acid.

Other excipients will include polyethylene glycol (PEG) or propylene glycol, and a non-ionic surfactant. The preferred PEG has a molecular weight of 300 to 400, most preferably 300 for parenteral formulations and 400 for oral formulations. PEG is included in the formulation at a ratio of between 100 to 10,000 parts by weight of PEG to each part by weight HLCD.

The preferred surfactant is a polysorbate-based compound, most preferably polysorbate-80 (PSB-80). The surfactant is included in the formulation at a range of 100 to 10,000 parts by weight of PSB to each part by weight HLCD. Most preferably the ratio is between 250 and 6500 parts by weight PSB per part of HLCD.

Parenteral formulations can optionally include a quantity of a lower alcohol, most preferably ethyl alcohol, and/or benzyl alcohol, and a lipid based excipient, preferably castor oil, most preferably an epoxylated castor oil such as Cremaphor-80.

The lower alcohol is incorporated into the formulation at between 0 to 5,000 parts by weight of each alcohol used per part by weight HLCD, with the maximum alcohol content being 10,000 parts by weight alcohol per part by weight of HLCD.

Lipid based excipient (Cremaphor-80) is incorporated into the formulation at between 0 to 10,000 parts by weight per part of HLCD.

Oral formulations will include the above ingredients and may optionally include a quantity of glycerol. Preferred ratio of glycerol is 0 to 5 parts by weight glycerol per part by weight of HLCD, most preferably 0.5 to 2.5 parts by weight per part by weight HLCD.

Oral formulations may further include an intestinal absorption facilitating compound, most preferably a bile acid such as taurocholic acid or a salt thereof at from 1 to 10 parts by weight per part by weight of HLCD. Oral formulations are also preferably formulated and incorporated into a pharmaceutically acceptable carrier, such as soft or hard gelatin capsules, among others, to facilitate swallowing.

Table 1 below illustrates a typical pharmaceutically acceptable formulation of HLCD/NMP adapted for parenteral administration to a patient.

TABLE 1

COMPONENT PARTS FOR PARENTERAL FORMULATIONS OF HLCD

| Ingredients | pts. by wt. |
| --- | --- |
| HLCD | 1 (1–40 mg/mL) |
| Ethyl Alcohol | 0 to 5,000 |
| Benzyl Alcohol | 0 to 5,000 |
| Acid | 100 to 5,000 |
| PEG 400 | 100 to 10,000 |
| NMP | 25 to 10,000 |
| Cremaphor-EL | 100 to 10,000 |
| Glycerol | 0 to 2.5 |
| Taurocholic Acid | 0 to 10 |
| Polysorbate 80 (Tween-80) | 100 to 10,000 |

Parenteral formulations are typically diluted with a common delivery solution such as 5% dextrose USP, lactated Ringer's solution or aqueous saline prior to administration to the patient.

Preferred oral formulations of HLCD/NMP are illustrated in Table 2 below.

TABLE 2

COMPONENT PARTS FOR ORAL FORMULATION OF HLCD

| Ingredients | pts. by wt. |
| --- | --- |
| HLCD | 1 (1–400 mg/mL) |
| NMP | 25 to 1000 |
| Citric Acid | 100 to 5,000 |
| EtOH | 100 to 5,000 |
| Polysorbate-80 (Tween-80) | 100 to 10,000 |
| PEG-400 | 100 to 10,000 |
| Glycerin | 0.5 to 2.5 |
| Taurocholic Acid | 1 to 10 |

Oral formulations are preferably encapsulated in a suitable carrier for oral delivery, typically gelatin capsules.

Preferred HLCD's used as active ingredients in the above formulations include camptothecin (CPT) and its derivatives which have a solubility of less than 5 micrograms per milliliter of water. Included in this group are CPT derivatives which have substitutions at one or more of the following positions on the molecule: [a] 7-substitutions; [b] 9-substitutions; [c] 10-substitutions; and [d] 11-substitutions; or any combination of the above in a di- or tri-substituted CPT derivative having a solubility of <5 $\mu$g/mL in water. Most preferred derivatives of CPT which fit into the category of HLCD are 10,11-methylenedioxy camptothecin, 10,11-ethylenedioxy camptothecin, 7-ethyl camptothecin, 7-ethyl-10-hydroxy camptothecin, 9-methyl camptothecin, 9-chloro-10,11-methylenedioxy camptothecin, 9-chloro camptothecin, 10-hydroxy camptothecin, 9,10-dichloro camptothecin, 10-bromo camptothecin, 10-chloro camptothecin, 9-fluoro camptothecin, 10-methyl camptothecin, 10-fluoro camptothecin, 9-methoxy camptothecin, 9-chloro-7-ethyl CPT, and 11-fluoro camptothecin. Other HLCDs will also fit the profile for the most preferred active compounds, and their inclusion into these formulations can be achieved with a minimum amount of experimentation.

The following specific examples illustrate the most preferred formulations which constitute this invention. These formulations are included to illustrate the best modes of making the formulations and are not introduced to limit the invention in any way.

EXAMPLES 1–2

Solubility of CPT and SN22 in NMP

A mixture of CPT (14 mg) and NMP (1 ml) was sonicated in a clean vial at 50 degrees Celsius for 30 minutes. The solution appeared clear and no precipitation or cloudiness appeared even after 72 hours at ambient temperature.

A mixture of SN22 (11.5 mg) and NMP (0.5 ml) was sonicated in a clean vial at 50 degrees Celsius for 30 minutes. The solution appeared clear and no precipitation or cloudiness appeared even after 1 week at ambient temperature.

Examples of NMP Formulation

Formulation #1

| | |
|---|---|
| Ethanol | 6.4 ml |
| Citric Acid | 1.0 g |
| PEG 300 | 50 g |
| NMP | 10.7 ml |
| TWEEN 80 | 10 g |

The above ingredients were mixed in the above order. First citric acid was dissolved in ethanol by sonication at 50 degrees Celsius for 30 minutes.

Formulation #2

| | |
|---|---|
| Ethanol | 20.3 ml |
| Benzyl Alcohol | 3.44 ml |
| Citric Acid | 4.0 g |
| PEG 300 | 40 g |
| NMP | 8.55 ml |
| TWEEN 80 | 8.0 g |

The above ingredients were mixed in the above order. First citric acid was dissolved in ethanol by sonication at 50 degrees Celsius for 30 minutes.

CPT in Formulation #1

Solutions of CPT in above Formulation #1 were prepared at concentrations of 0.3, 0.4, and 0.5 mg of CPT in 1 ml of formulation. The mixtures were sonicated at 50 degrees Celsius for 60 min. There were no cloudiness, suspension or precipitation. The mixtures were filtered through 0.2 micron filter. The mixtures were diluted with 0.9% sodium chloride solution and studied for the appearance of Tyndall effect as given in the following tables:

TABLE 1

CPT 0.3 mg/ml of formulation #1 dilution with 0.9% NaCl solution

| Dilution | 0 min | 15 min | 30 min | 45 min | 60 min | 90 min | 120 min | 1 day |
|---|---|---|---|---|---|---|---|---|
| 1:1 | clear | clear | clear | clear | clear | clear | clear | — |
| 1:2 | clear | clear | clear | clear | clear | clear | clear | — |
| 1:5 | clear | clear | clear | clear | clear | clear | clear | — |
| 1:10 | clear | clear | clear | clear | clear | clear | clear | — |
| 1:100 | clear | clear | clear | clear | clear | clear | clear | clear |

TABLE 2

CPT 0.4 mg/ml of formulation #1 dilution with 0.9% NaCl solution

| Dilution | 0 min | 15 min | 30 min | 45 min | 60 min | 90 min | 120 min | 1 day |
|---|---|---|---|---|---|---|---|---|
| 1:1 | clear | clear | clear | clear | clear | clear | clear | — |
| 1:2 | clear | clear | clear | clear | clear | clear | clear | — |
| 1:5 | clear | clear | clear | clear | clear | clear | clear | — |
| 1:10 | clear | clear | — | — | — | — | — | — |
| 1:100 | clear | clear | clear | clear | clear | clear | clear | clear |

TABLE 3

CPT 0.5 mg/ml of formulation #1 dilution with 0.9% NaCl solution

| Dilution | 0 min | 15 min | 30 min | 45 min | 60 min | 90 min | 120 min | 1 day |
|---|---|---|---|---|---|---|---|---|
| 1:1 | clear | clear | clear | clear | clear | clear | — | — |
| 1:2 | clear | clear | clear | clear | clear | — | — | — |
| 1:5 | clear | clear | clear | clear | — | — | — | — |
| 1:10 | clear | clear | — | — | — | — | — | — |
| 1:100 | clear | clear | clear | clear | clear | clear | clear | clear |

SN22 in Formulation #1

Solutions of SN22 in above Formulation #1 were prepared at concentrations of 0.5, 0.6, 0.7 and 1.0 mg of SN22 in 1 ml of formulation. The mixtures were sonicated at 50 degrees Celsius for 60 min. There were no cloudiness, suspension or precipitation. The mixtures were filtered through 0.2 micron filter. The mixtures were diluted with 0.9% sodium chloride solution and studied for the appearance of Tyndall effect as given in the following tables:

TABLE 4

SN22 0.5 mg/ml of formulation #1 dilution with 0.9% NaCl solution

| Dilution | 0 min | 15 min | 30 min | 45 min | 60 min | 90 min | 120 min | 1 day |
|---|---|---|---|---|---|---|---|---|
| 1:1 | clear | clear | clear | clear | clear | clear | clear | clear |
| 1:2 | clear | clear | clear | clear | clear | clear | clear | clear |
| 1:5 | clear | clear | clear | clear | clear | clear | clear | clear |
| 1:10 | clear | clear | clear | clear | clear | clear | clear | clear |
| 1:100 | clear | clear | clear | clear | clear | clear | clear | clear |

TABLE 5

SN22 0.6 mg/ml of formulation #1 dilution with 0.9% NaCl solution

| Dilution | 0 min | 15 min | 30 min | 45 min | 60 min | 90 min | 120 min | 1 day |
|---|---|---|---|---|---|---|---|---|
| 1:1 | clear | clear | clear | clear | clear | clear | clear | clear |
| 1:2 | clear | clear | clear | clear | clear | clear | clear | clear |
| 1:5 | clear | clear | clear | clear | clear | clear | clear | clear |
| 1:10 | clear | clear | clear | clear | clear | clear | clear | clear |
| 1:100 | clear | clear | clear | clear | clear | clear | clear | clear |

TABLE 6

SN22 0.7 mg/ml of formulation #1 dilution with 0.9% NaCl solution

| Dilution | 0 min | 15 min | 30 min | 45 min | 60 min | 90 min | 120 min | 1 day |
|---|---|---|---|---|---|---|---|---|
| 1:1 | clear | clear | clear | clear | clear | clear | clear | clear |
| 1:2 | clear | clear | clear | clear | clear | clear | clear | clear |
| 1:5 | clear | clear | clear | clear | clear | clear | clear | clear |
| 1:10 | clear | clear | clear | clear | clear | clear | clear | clear |
| 1:100 | clear | clear | clear | clear | clear | clear | clear | clear |

TABLE 7

SN22 1.0 mg/ml of formulation #1 dilution with 0.9% NaCl solution

| Dilution | 0 min | 15 min | 30 min | 45 min | 60 min | 90 min | 120 min | 1 day |
|---|---|---|---|---|---|---|---|---|
| 1:1 | clear | clear | clear | clear | clear | clear | clear | clear |
| 1:2 | clear | clear | clear | clear | clear | clear | clear | — |
| 1:5 | clear | clear | clear | clear | clear | clear | clear | — |
| 1:10 | clear | clear | — | — | — | — | — | — |
| 1:100 | clear | clear | clear | clear | clear | clear | clear | clear |

It should be noted that these formulations are only examples of the preferred embodiment of this invention and not limiting of the invention in any way. The scope of the invention is defined by the following claims.

What is claimed is:

1. A pharmaceutical formulation adapted for oral or parenteral administration to a patient, said formulation comprising:
   a) a pharmaceutically effective amount of a highly lipophilic, poorly water soluble camptothecin derivative;
   b) a sufficient volume of N-methyl pyrrolidin-2-one to dissolve all of said camptothecin derivative and form a solution; and
   c) an excipient comprising a pharmaceutically acceptable acid, said acid added to said solution in an amount sufficient to lower the pH of said solution to between 2.0–6.0.

2. The pharmaceutical formulation of claim 1 wherein said formulation further comprises one or more additional pharmaceutically acceptable excipients.

3. The pharmaceutical formulation of claim 2 wherein said additional excipients are selected from the group consisting of a polyethylene glycol, epoxylated castor oil, ethyl alcohol, benzyl alcohol, an intestinal absorption facilitating compound, a non-ionic surfactant, and glycerin.

4. The pharmaceutical formulation of claim 3, wherein said intestinal absorption facilitating compound is taurocholic acid or a pharmaceutically acceptable salt thereof.

5. A pharmaceutical formulation adapted for oral or parenteral administration to a patient, said formulation comprising:
   a) a pharmaceutically effective amount of a highly lipophilic, poorly water soluble camptothecin derivative;
   b) a sufficient volume of N-methyl pyrrolidin-2-one to form a liquid suspension with said camptothecin derivative; and
   c) an excipient comprising a pharmaceutically acceptable acid, said acid added to said solution in an amount sufficient to lower the pH of said suspension to between 2.0–6.0.

6. The formulation of claim 5 wherein said formulation further comprises one or more additional pharmaceutically acceptable excipients.

7. The formulation of claim 6 wherein said additional excipients are selected from the group consisting of a polyethylene glycol, epoxylated castor oil, ethyl alcohol, benzyl alcohol, an intestinal absorption facilitating compound, a non-ionic surfactant, and glycerin.

8. The pharmaceutical formulation of claim 7 wherein said intestinal absorption facilitating compound is taurocholic acid or a pharmaceutically acceptable salt thereof.

9. A pharmaceutical formulation comprising one part by weight/mL of a highly lipophilic poorly water soluble camptothecin derivative having a water solubility of less than 5 $\mu$g/mL, at a concentration of 1.0 mg/mL–40.0 mg/mL of a solution or suspension. wherein each mL of said solution or suspension further comprises:
   a) 1,000–10,000 parts by weight of N-methylpyrrolidinone;
   b) 100–5,000 parts by weight of a pharmaceutically acceptable acid;
   c) 0–10.0 parts by weight of an intestinal absorption facilitating compound which is taurocholic acid or a pharmaceutically acceptable salt thereof;
   d) 0–2.5 parts by weight of glycerol;
   e) 1000–10,000 parts by weight of a polyethylene glycol;
   f) 1,000–5,000 parts by weight of ethyl alcohol or benzyl alcohol or a combination of ethyl alcohol and benzyl alcohol;
   g) 1,000–10,000 parts by weight of a non-ionic surfactant; and
   h) 0–10,000 parts by weight of epoxylated castor oil.

10. The formulation of claim 11 wherein said formulation is an oral formulation, said taurocholic acid or salt thereof is present from 1.0–10.0 parts by weight, said glycerol is present from 0.5–2.5 parts by weight, said epoxylated castor oil is present from 1,000–10,000 parts by weight, and wherein said forulation is further encapsulated within a swallowable carrier.

11. The formulation of claim 9 wherein said non-ionic surfactant is polysorbate-80.

12. The formulation of either of claim 9, wherein said formulation is diluted with a pharmaceutically acceptable diluent to form a deliverable solution, wherein the concentration of said camptothecin derivative within said solution is from 0.001 mg/mL to 1.0 mg/mL.

* * * * *